Figure 1:
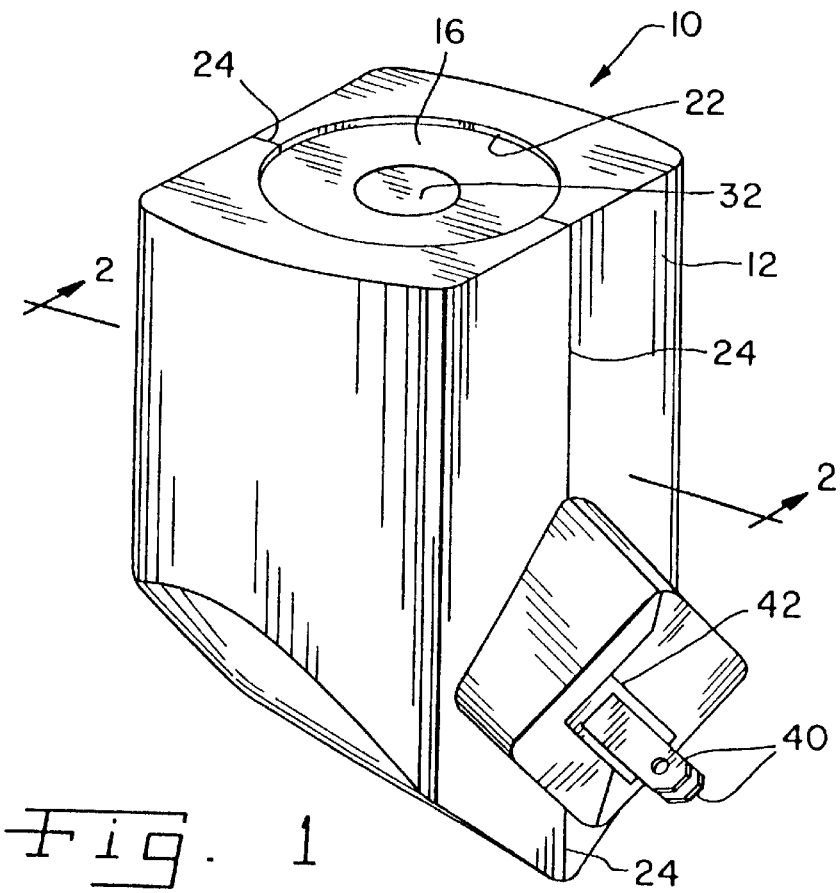
Figure 2:
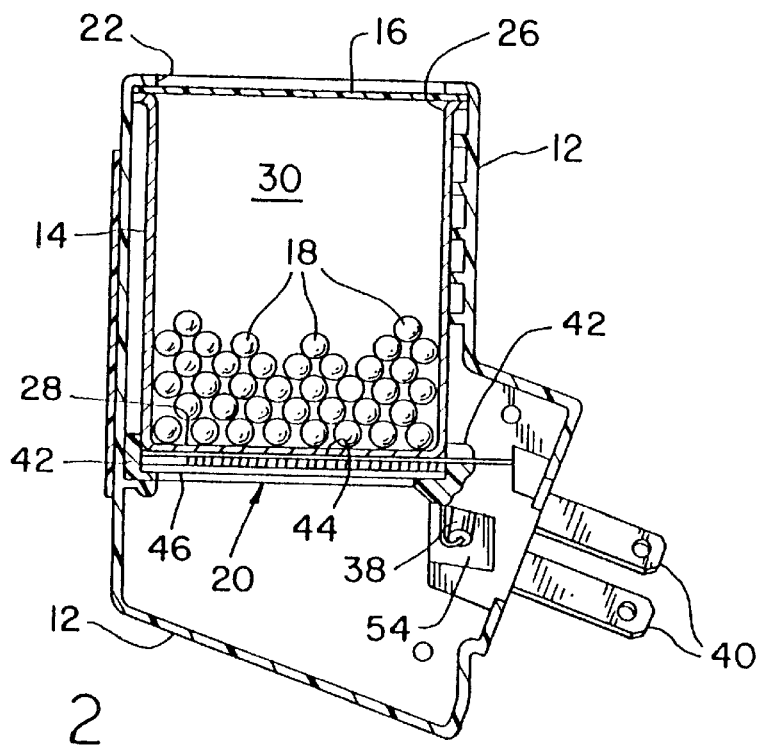

United States Patent
Smith et al.

[11] Patent Number: 6,151,827
[45] Date of Patent: *Nov. 28, 2000

[54] ELECTRICALLY HEATED INSECTICIDE DELIVERY SYSTEM

[75] Inventors: Kevin W. Smith, North Webster; Edgar S. Haffner, Syracuse, both of Ind.

[73] Assignee: Heaters Engineering, Inc., North Webster, Ind.

[ * ] Notice: Under 35 U.S.C. 154(b), the term of this patent shall be extended for 12 days.

[21] Appl. No.: 08/663,471

[22] Filed: Jun. 13, 1996

[51] Int. Cl.⁷ .................................................. A01M 19/00
[52] U.S. Cl. ................................................................. 43/129
[58] Field of Search .................................................. 43/129

[56] References Cited

U.S. PATENT DOCUMENTS

| | | | |
|---|---|---|---|
| 1,982,358 | 11/1934 | Smith | 43/129 |
| 2,513,919 | 7/1950 | Costello | 43/129 |
| 2,616,024 | 10/1952 | Laibow | 43/129 |
| 2,660,828 | 12/1953 | Abrams | 43/129 |
| 3,290,112 | 12/1966 | Gillenwater | 43/129 |
| 3,421,841 | 1/1969 | Wittwer | 43/129 |
| 3,778,924 | 12/1973 | Okui | 43/129 |
| 4,037,352 | 7/1977 | Hennart | 43/129 |
| 4,214,146 | 7/1980 | Schimanski | 43/129 |
| 4,228,124 | 10/1980 | Kashihara | 43/129 |
| 4,425,302 | 1/1984 | Pons Pons | 43/129 |
| 4,467,177 | 8/1984 | Zobele | 43/129 |
| 4,675,504 | 6/1987 | Suhajda | 43/129 |
| 4,687,904 | 8/1987 | Melanson | 43/129 |
| 5,168,654 | 12/1992 | Chien | 43/129 |
| 5,282,334 | 2/1994 | Kimura | 43/129 |

FOREIGN PATENT DOCUMENTS

| | | | |
|---|---|---|---|
| 556003 | 4/1957 | Belgium | 43/129 |
| 498286 | 12/1953 | Canada | 43/129 |
| 542572 | 6/1957 | Canada | 43/129 |
| 761026 | 11/1956 | United Kingdom | 43/129 |

*Primary Examiner*—Kurt Rowan
*Attorney, Agent, or Firm*—Taylor & Aust, P.C.

[57] ABSTRACT

The invention is directed to an insecticide delivery system for delivering an insecticide to an ambient environment. The insecticide delivery system includes a can having an open end and an interior. A thermally activated insecticide is disposed within the can interior. An electrical heater assembly is disposed adjacent to the can. The heater assembly is configured for increasing a temperature of the can to a temperature whereby the thermally activated insecticide is delivered to the ambient environment. The heater assembly includes a resistance heater wire connected in series with a thermal cut-off device. The resistance heater wire may include a parallel shunt at one or both ends thereof.

15 Claims, 2 Drawing Sheets

ELECTRICALLY HEATED INSECTICIDE DELIVERY SYSTEM

BACKGROUND OF THE INVENTION

1. Field of the Invention

The present invention relates to an insecticide delivery system, and, more particularly, to an insecticide delivery system having an insecticide which is disposed within a can and selectively discharged into the ambient environment.

2. Description of the Related Art

It is known to provide a carrier within an enclosed canister for delivery of an insecticide to the ambient environment. For example, it is known to provide an aerosol carrier within a canister under pressure having an active insecticide ingredient therein. The discharge nozzle of the canister may be locked into place such that the aerosol carrier delivers the insecticide to the ambient environment. Typically, such an apparatus is used inside of a building to rid the interior of the building of particular insects. The active insecticide within the canister can vary depending upon the particular types of undesirable insects within the building.

A problem with an aerosol canister as described above is that the aerosol essentially produces a fog within the interior of the building. The fog includes liquid droplets which are relatively quickly pulled via gravitational force to the floor of the building. The treated area of coverage using such an aerosol fogger is thus relatively limited. Another problem is that such an aerosol fogger may include volatile organic components which are combustible. In the presence of a spark or open flame, such volatile components could possibly ignite or explode.

It is also known that smoke carries an active chemical ingredient such as an insecticide better than an aerosol carrier. The smoke travels better within the interior of a building, and also penetrates better into cracks, grooves, etc.

One known method of generating smoke for use with an insecticide involves the use of a chemical reaction within a canister which heats a thermally activated insecticide. The thermally activated insecticide produces a smoke carrier and an active insecticide upon reaching a predetermined temperature.

What is needed in the art is an insecticide delivery system which utilizes smoke as a carrier and does not require the use of a chemical reaction to generate heat and activate a thermally activated insecticide.

SUMMARY OF THE INVENTION

The present invention provides an electrically heated insecticide delivery system wherein an electrical heater assembly is disposed adjacent to a can and thermally activates an insecticide disposed therein. The electrical heater assembly includes a resistance heater wire having a parallel shunt at each end thereof, and a thermal cut-off device connected in series with the resistance heater wire.

The invention comprises, in one form thereof, an insecticide delivery system for delivering an insecticide to an ambient environment. The insecticide delivery system includes a can having an open end and an interior. A thermally activated insecticide is disposed within the can interior. An electrical heater assembly is disposed adjacent to the can. The heater assembly is configured for increasing a temperature of the can to a temperature whereby the thermally activated insecticide is delivered to the ambient environment. The heater assembly includes a resistance heater wire connected in series with a thermal cut-off device.

The resistance heater wire may include a parallel shunt at one or both ends thereof.

An advantage of the present invention is that a redundant thermal cut-off is provided.

Another advantage is that each end of the resistance heater wire is formed as a cold end.

Yet another advantage is that the electrical heater assembly is manufactured by an overmolding process.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of an embodiment of an insecticide delivery system of the present invention;

FIG. 2 is a side, sectional view taken along line 2—2 in FIG. 1;

FIG. 3 is a plan view of an embodiment of a resistance heater wire, thermal cut-off device and blades which form part of an electrical heater assembly of the present invention;

FIG. 4 is an end view of an embodiment of the electrical heater assembly of the present invention; and FIG. 5 is a sectional view of the electrical heater assembly shown in FIG. 4, taken along line 5—5.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, and more particularly to FIGS. 1 and 2, there is shown an embodiment of a chemical delivery system 10 for delivering a chemical to an ambient environment. In the embodiment shown, chemical delivery system 10 is in the form of an insecticide delivery system 10. Insecticide delivery system 10 generally includes a housing 12, can 14, thermally rupturable seal 16, thermally activated chemical 18, and electrical heater assembly 20.

Housing 12 carries and supports can 14 and electrical heater assembly 20. Housing 12 includes an opening 22 at an end thereof which is disposed adjacent to seal 16. Housing 12 may be formed from a plastic injection molding process, and may include a split line 24 for providing access to the interior thereof.

Can 14 has an open end 26 and a closed end 28 disposed opposite open end 26. Can 14 also defines an interior 30 for receiving thermally activated chemical 18 therein. Can 14 is formed from a thermally conductive material, and preferably is formed from a metallic material.

Thermally rupturable seal 16 is attached to and closes open end 26 of can 14. In the embodiment shown, seal 16 is formed from a material consisting essentially of polyethylene. Heat which is conducted through can 14 (as will be described hereinafter) increases the temperature of seal 16 which melts at a predetermined temperature dependent upon the physical characteristics of the material from which seal 16 is constructed. Seal 16 may include a transparent window 32 (FIG. 1) such that a user may easily view thermally activated chemical 18 disposed within can 14.

Thermally activated chemical 18 disposed within can interior 30 is in the form of a thermally activated insecticide. In the embodiment shown, thermally activated insecticide 18 is manufactured as a pelletized or granulized insecticide. For one anticipated embodiment, thermally activated insecticide 18 has an active ingredient consisting essentially of pelletized permethrin. However, other types of chemicals or insecticides may be used within can interior 30. Thermally activated insecticide 18 undergoes a chemical reaction when the temperature thereof reaches a predetermined temperature. For example, in the case where thermally activated insecticide 18 is in the form of permethrin, a chemical reaction occurs at approximately 275° C.

Referring now to FIGS. 2–5, electrical heater assembly 20 will be described in greater detail. Heater assembly 20 is disposed adjacent to closed end 28 of can 14 and is configured for increasing a temperature of can 14 to a temperature whereby thermally activated insecticide 18 is activated and delivered to the ambient environment. In general, heater assembly 20 includes a resistance heater wire 36, thermal cut-off (TCO) device 38, blades 40, body 42, and mica sheets 44, 46.

Figure 3:
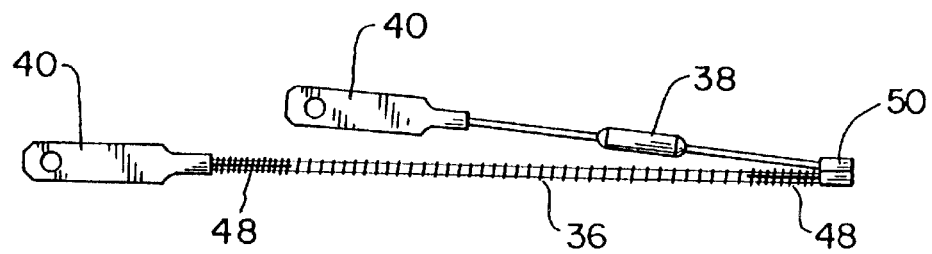

Resistance heater wire 36, in the embodiment shown, is in the form of a conductive wire which is wrapped in a spiral manner about a non-conductive core (not numbered). The length, diameter and material of resistance heater wire 36 wrapped about the core determines the resistance thereof, and thus the heat generated thereby. Referring to FIG. 3, resistance heater wire 36 includes a "cold end" at each end thereof which is not heated and which may be imbedded within body 42. In particular, resistance heater wire 36 includes a parallel shunt 48 at each end thereof which overlaps a portion of resistance heater wire 36. Shunt 48 is constructed of a conductive material which has a lower resistance than that of the resistance heater wire 36 wrapped about the core. Each conductive shunt 48 in essence defines a bypass through which electrical current flows during operation and thereby prevents each associated end of resistance heater wire 36 from being heated. Resistance heater wire 36 wrapped around the core may be of any suitable material. In the embodiment shown, resistance heater wire 36 consists essentially of nickel-chromium.

TCO device 38 is connected in series with resistance heater wire 36 using a connector 50 (FIG. 3). TCO device 38 has a thermal cut-off temperature which is dependent upon a temperature at which a chemical reaction of thermally activated insecticide 18 occurs. For example, if thermally activated insecticide 18 is in the form of permethrin having a chemical reaction which occurs at approximately 275° C., TCO device 38 accordingly has a thermal cut-off at a temperature which is dependent upon the 275° C. thermal activation temperature of the permethrin. Above the thermal cut-off temperature, TCO device 38 prevents electrical current from flowing therethrough.

Blades 40 are connected to opposite ends of resistance heater wire 36 and TCO device 38. That is, each blade 40 is connected to a respective end of resistance heater wire 36 and TCO device 38 which is opposite from connector 50. Blades 40 provide electrical connection with an AC power source (not shown), such as a common 115 VAC household electrical current. Blades 40 are carried within body 42, which in turn may be carried by housing 12 such that insecticide delivery system 10 may be utilized with a 115 VAC electrical outlet having slots disposed in either a horizontal or vertical orientation.

TCO device 38 and resistance heater wire 36 define a primary and a secondary thermal cut-off for heater assembly 20, respectively. TCO device 38 prevents electrical current from flowing therethrough in the manner as described above. Resistance heater wire 36 provides a secondary thermal cut-off by melting if the temperature thereof reaches a predetermined temperature. For example, resistance heater wire 36 may be formed from a nickel-chromium material having a melting temperature of approximately 1395° C. If TCO device 38 does not function properly and the temperature of resistance heater wire 36 continues to increase, resistance heater wire 36 melts and thereby breaks the electrical circuit to prevent electrical current from flowing therethrough.

Figure 4:
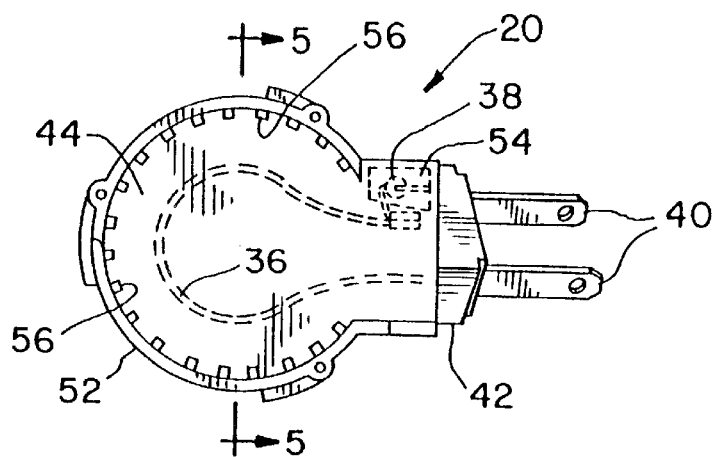
Figure 5:
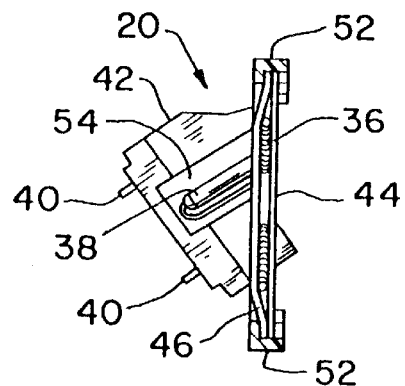

Resistance heater wire 36, TCO device 38 and blades 40 are overmolded using a plastic injection molding process. The injected plastic defines body 42 which carries each of resistance heater wire 36, TCO device 38 and blades 40. Body 42 includes a ring 52 disposed radially outward of resistance heater wire 36 (FIG. 4). Body 42 also includes a cavity 54 (FIGS. 2 and 4) formed in a side thereof which is generally opposite from can 14. TCO device 38 is disposed within cavity 54 and is thus open to the atmosphere within housing 12 below heater assembly 20. The temperature within housing 12 below heater assembly 20 thus acts upon TCO device 38 during operation.

Mica sheet 44 is disposed between can 14 and resistance heater wire 36 of heater assembly 20. Mica sheet 44 is configured with a thickness so as to be essentially thermally conductive and electrically non-conductive. Thus, heat generated by heater assembly 20 is conducted to can 14, while can 14 is electrically insulated from heater assembly 20. Mica sheet 44 is disposed radially inward of ring 52 of body 42, and is held in place by a plurality of fingers 56 (FIG. 4) extending from ring 52.

Mica sheet 46 is constructed similar to mica sheet 44, except with a greater thickness. The greater thickness provides mica sheet 46 with essentially thermal and electrical non-conductivity. The thermal non-conductivity may be desirable since mica sheet 46 is disposed on a side of resistance heater wire 36 which is opposite from can 14.

In operation, blades 40 of insecticide delivery system 10 are plugged into a 115 VAC electrical outlet. Insecticide delivery system 10 is plugged into either a horizontal or vertically oriented electrical outlet such that opening 22 of housing 12 is disposed substantially at the top end of housing 12. Electrical current flowing through resistance heater wire 36 causes the generation of heat, which is transferred through mica sheet 44 to can 14. The temperature of can 14 thus increases as heat is applied thereto to a predetermined temperature at which seal 16 melts and exposes open end 26 of can 14. At another predetermined temperature, a chemical reaction of thermally activated insecticide 18 takes place which causes the production of smoke carrying the active insecticide to be discharged from open end 26 of can 14. At a temperature above which the chemical reaction of thermally activated insecticide 18 takes place, TCO device 38 opens to prevent electrical current from thereafter flowing therethrough. In the event that TCO device 38 malfunctions, resistance heater wire 36 subsequently melts to open the electrical circuit and prevent electrical current from passing therethrough. Insecticide delivery system 10 can then be disconnected from the 115 VAC electrical outlet and discarded.

In the embodiment of the present invention shown in the drawings and described above, electrical heater assembly 20 includes a resistance heater wire for heating the thermally activated insecticide. However, it is also to be understood that other types of heaters may be utilized within the electrical heater assembly. For example, it is possible to replace the resistance heater wire with a Printed Thick Film (PTF) heater which is used for heating the thermally activated insecticide. More particularly, the PTF heater includes a ceramic/metal (cermet) ink which is deposited on a layer of mica. The cermet ink is a resistive ink which produces heat upon passing an electrical current therethrough. The cermet ink is connected to conductive electrical terminals at predetermined locations, which are in turn connected to the source of electrical current. One of the electrical terminals is connected in series with a TCO device, as described above. An insulating layer of mica is placed over the cermet ink, and the assembly is overmolded using a plastic injection molding process. The TCO and cermet ink are configured to open the circuit redundantly with the TCO functioning as the primary shut-off and the cermet ink functioning as the secondary shut-off. Rather than using cermet ink as the resistive ink, it is also possible to use a polymer ink which is silk screened onto a plastic or ceramic substrate.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A chemical delivery system for delivering a chemical to an ambient environment, said chemical delivery system comprising:

a can having an open end and an interior;

a thermally activated chemical disposed within said can interior;

an electrical heater assembly disposed adjacent to said can, said heater assembly configured for increasing a temperature of said can to a temperature whereby said thermally activated chemical is delivered to the ambient environment, said heater assembly including a resistance heater wire connected with a thermal cut-off device; and a thermally rupturable seal closing said open end of said can.

2. The chemical delivery system of claim 1, wherein said seal consists essentially of polyethylene.

3. The chemical delivery system of claim 1, manufactured by the process of overmolding said electrical heater assembly.

4. The chemical delivery system of claim 3, wherein said heater assembly further comprises an essentially thermally conductive and electrically non-conductive sheet disposed between said resistance heater wire and said can.

5. The chemical delivery system of claim 4, wherein said sheet is comprised of a material consisting essentially of mica.

6. The chemical delivery system of claim 3, wherein said heater assembly further comprises an essentially thermally and electrically non-conductive sheet disposed adjacent to said resistance heater wire on a side of said resistance wire opposite said can.

7. The chemical delivery system of claim 6, wherein said sheet is comprised of a material consisting essentially of mica.

8. A chemical delivery system for delivering a chemical to an ambient environment, said chemical delivery system comprising:

a can having an open end and an interior;

a thermally activated chemical disposed within said can interior; and an electrical heater assembly disposed adjacent to said can, said heater assembly configured for increasing a temperature of said can to a temperature whereby said thermally activated chemical is delivered to the ambient environment, said heater assembly including a resistance heater wire having a parallel shunt at one end thereof which bypasses a portion of said heater wire.

9. The chemical delivery system of claim 8, wherein said resistance heater wire further has a parallel shunt at an opposing end thereof which bypasses a portion of said heater wire.

10. The chemical delivery system of claim 9, wherein said electrical heater assembly further comprises a thermal cut-off device connected in series with said resistance heater wire.

11. The chemical delivery system of claim 8, further comprising a housing, said can and said heater assembly disposed within and carried by said housing.

12. The chemical delivery system of claim 8, wherein said thermally activated chemical comprises an insecticide.

13. The chemical delivery system of claim 8, wherein said can includes a closed end opposite said open end, and wherein said heater assembly is disposed adjacent to said closed end.

14. The chemical delivery system of claim 8, further comprising a thermally rupturable seal closing said open end of said can.

15. The chemical delivery system of claim 14, wherein said seal consists essentially of polyethylene.

* * * * *